US00PP34781P2

(12) United States Plant Patent
Townsend

(10) Patent No.: US PP34,781 P2
(45) Date of Patent: Nov. 29, 2022

(54) HOP PLANT NAMED 'IH101033'

(50) Latin Name: ***Humulus lupulus* L.**
Varietal Denomination: IH101033

(71) Applicant: Indie Hops, LLC, Portland, OR (US)

(72) Inventor: Michael Shaun Townsend, Corvallis, OR (US)

(73) Assignee: Indie Hops, LLC, Portland, OR (US)

( * ) Notice: Subject to any disclaimer, the term of this patent is extended or adjusted under 35 U.S.C. 154(b) by 0 days.

(21) Appl. No.: 17/575,582

(22) Filed: Jan. 13, 2022

(51) Int. Cl.
*A01H 5/02* (2018.01)
*A01H 6/28* (2018.01)

(52) U.S. Cl.
USPC ..... Plt./236

(58) Field of Classification Search
USPC ..... Plt./236
CPC ... A01H 5/02; A01H 5/08; A01H 5/00; A01H 6/28; A01H 6/00; A01H 5/12
See application file for complete search history.

(56) References Cited

PUBLICATIONS

Indie Hops Archive, A hora do Strata: Learn about the hop that has become one of the most appreciated in Brazil, 2021, retrieved on Mar. 1, 2022, retrieved from the Internet at https://lupulado-com.translate.goog/category/indie-hops/?_x_tr_sch=http&_x_tr_sl=pt&_x_tr_tl=en&_x_tr_hl=en&_x_tr_pto=sc, 18 pp. (Year: 2021).*
The Northwest Beer Guide, Lorien, retrieved on Mar. 1, 2022, retrieved from the Internet at https://www.northwestbeerguide.com/hops/category/L%C3%B3rien, one page. (Year: 2021).*
IHGC retrieved on Mar. 1, 2022, retrieved from the Internet at http://www.hmelj-giz.si/ihgc/doc/2021_NOV_IHGC_HopVarietyList21.pdf, one page. (Year: 2021).*

* cited by examiner

*Primary Examiner* — June Hwu
(74) *Attorney, Agent, or Firm* — Klarquist Sparkman, LLP

(57) ABSTRACT

A new and distinct hop plant cultivar named 'IH101033' is disclosed, characterized by having an early maturity date in Oregon's Willamette Valley; tolerance to downy mildew (*Pseudoperonospora humuli* [Miyabe & Takah.] G. W. Wilson); vigor with potentially high yield; low alpha acids content; typically high beta acids content; low total essential oil content; and unique amounts of 19 essential oil components implicated in beer flavor and aroma.

4 Drawing Sheets

Genus and species: *Humulus lupulus* L.
Variety denomination: 'IH101033'.

BACKGROUND

The present disclosure comprises a new and distinct cultivar of *Humulus lupulus* L., and hereinafter referred to by the cultivar name 'IH101033'.

The new hop plant resulted from a planned breeding program from crossing *Humulus lupulus* 'Sterling' (unpatented) as the female parent to the male parent *Humulus lupulus* '64035M', an unpatented hop male genotype released by the USDA-ARS hop breeding and genetics program based in Corvallis, Oreg. in 1985. The resulting hop plant was selected when growing in a greenhouse in Corvallis, Oreg. during February 2011.

SUMMARY

In July 2010, a cross was made between the female hop cultivar 'Sterling' and the male hop '64035M' near Corvallis, Oreg. (FIG. 1). Both parents are publicly available genotypes released by the USDA-ARS hop breeding program located near Corvallis (Haunold et al., 1985, Registration of USDA 64035M male hop germplasm. Crop Sci. 25:889-890; Henning and Haunold, 1999, Notice of release of 'Sterling', a high-yielding Saazer-type hop cultivar. United States Dept. of Agriculture, Washington, D.C.). Seed was collected by hand, stratified at 34° F. for eight weeks, and planted into flats containing a standard soil mix in a greenhouse in Corvallis, Oreg. during January 2011. Established hop seedlings were evaluated for powdery mildew (*Podosphaera macularis* [Walk.] U. Braun & S. Takam) resistance and general vigor, and 'IH101033' was one of the seedlings selected and transplanted into 1-gallon pots. Once established, potted plants were subsequently transplanted into a field nursery near Corvallis, Oreg. during May 2011 and given a 4' bamboo stake to climb on during that growing season. 'IH101033' was evaluated for downy mildew (*Pseudoperonospora humuli* [Miyabe & Takah.] G. W. Wilson) and powdery mildew during 2012, 2013, 2014, and 2015 at Corvallis. Due to transient outbreaks, 'IH101033' was evaluated for hop looper (*Hypnea humuli* Harris) damage in 2013 and 2014 and Damson hop aphid (*Phorodon humuli* Schrank) damage in 2014. The sex of this genotype was determined to be female in 2012. Yield potential and preliminary sensory evaluations were initially evaluated in 2014 and 2015 when the single plant was harvested.

Based upon agronomic performance and the initial sensory assessment, 'IH101033' was propagated via rhizomes obtained from the individual mother plant in February 2015 with additional propagation from stem cuttings in a greenhouse. Plants were established in 1-gallon pots and transplanted into replicated field nurseries on two commercial hop farms in Oregon's Willamette Valley during the summer of 2015. These nurseries were managed by the two farms using their normal hop production techniques. Due to the growers utilizing aggressive pest and pathogen control measures, only yield, chemistry, and sensory data were collected from these plots for 2017, 2019, 2020, and 2021. Beginning in September 2017, 'IH101033' entered into sensory evaluations by small, organized groups of craft brewers, primarily in the U.S. Pacific Northwest, although select breweries outside this region were also used. Sensory analysis consisted primarily of dry-rub evaluations, along with the hops "dry hopped" into beer at a small bench top scale using a commercial Kolsch style beer that is balanced with hop bitterness but has no hop aroma or flavor, thus allowing the hops from 'IH101033' to impart their unique aroma and flavor characteristics into the beer for sensory evaluation. Small scale pilot brews by breweries were also used to evaluate the hop character when used not only in dry-hopping, but also on the "hot side" of the brewing process.

In 2019, 'IH101033' was propagated and established in a 3.7 acre block near Silverton, Oreg., and a 6 acre block near Independence, Oreg. These blocks were managed and harvested by the two cooperating hop growers. A test crop was produced from each plot in 2020 and 2021, processed by a hop merchant in Portland, Oreg., and 96 craft brewers have created test beers to evaluate hop aroma and flavor profiles from 'IH101033' hops over a wide range of brewing styles.

The 'IH101033' hop variety is distinguished from other hop varieties due to the following unique combination of agronomic and chemical characteristics. When grown in Oregon's Willamette Valley, 'IH101033' is:

1. slightly early to mature (August 22-24);
2. tolerant of downy mildew;
3. vigorous with potentially high yield (Table 1);
4. has low alpha acids content (Tables 2, 3, 4);
5. typically has high beta acids (Tables 2, 3, 4);
6. has low total essential oil content (Tables 2, 3, 4); and
7. contains unique amounts of 19 essential oil components implicated in beer flavor and aroma (Tables 5, 6, 7).

Asexual reproduction of the new hop variety 'IH101033' was first performed in Corvallis, Oreg. via rhizomes in 2015. Subsequent propagations have been via rhizomes and stem cuttings, and this variety has remained genetically stable.

DETAILED BOTANICAL DESCRIPTION

Figure 1:
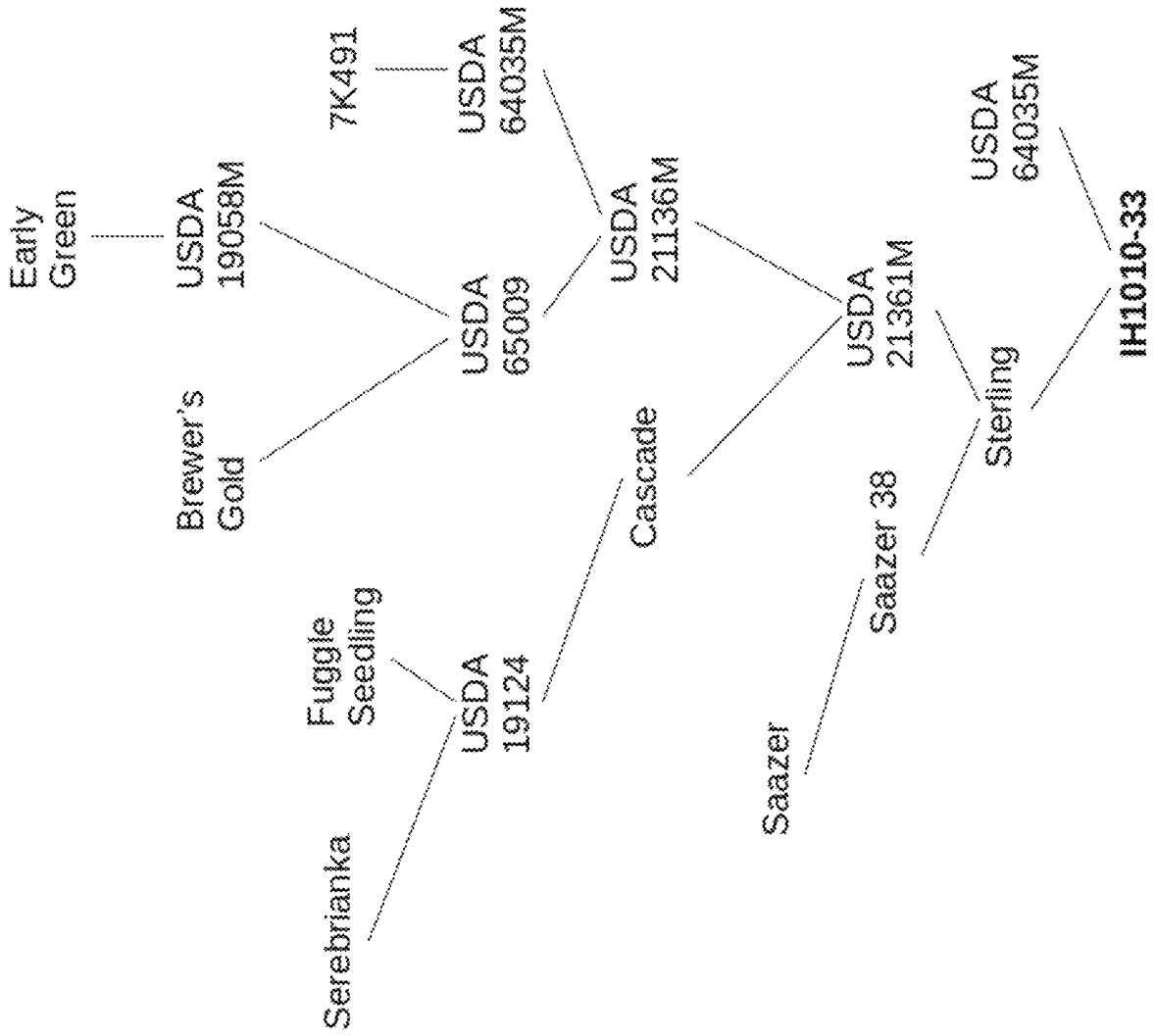
FIG. 1 illustrates the pedigree for 'IH101033'.

The following detailed description of the 'IH101033' variety is based on observations of various 2-6-year old plants, 2nd propagation generation, growing on a commercial hop farm in the Willamette Valley of Oregon between 2017 and 2021. The plants were 2 years old when first evaluated in 2017, and 6 years old by 2021. The original plant has been observed growing in a cultivated area in Corvallis, Oreg. The new cultivar has not been evaluated under all possible environmental conditions but was developed for Oregon's Willamette Valley (USDA hardiness zone 8b near 45 degrees North latitude). Certain characteristics of this variety, such as growth and color, may change with changing environmental conditions (e.g., light, temperature, moisture, nutrient availability, or other factors). The color descriptions are all based on *The Royal Horticultural Society Colour Chart,* 6$^{th}$ edition, 2015.

Parentage:

*Female parent.—Humulus lupulus* 'Sterling'.

*Male parent.—Humulus lupulus* '64035M'.

COMPARISON TO FEMALE PARENT AND OTHER COMMERCIALLY AVAILABLE VARIETIES

Tables 1-7 below provide comparisons between various traits of the 'IH101033' variety, the female parent 'Sterling', the standard Oregon aroma hop cultivar 'Cascade' (unpatented), and 'OR91331' (U.S. Plant Pat. No. 31,042). As shown in Table 1, 'IH101033' is vigorous with potentially higher yield than 'Sterling', 'Cascade', and 'OR91331'.

TABLE 1

Per-plant yield for 'IH101033' over four years at a commercial hop farm in the Willamette Valley of Oregon.

| Genotype | Yield (lbs)† | Range (lbs) |
|---|---|---|
| 2017 | | |
| 'IH101033' | 9.37 a | 3.40-8.24 |
| 'Sterling' | 6.18 ab | 5.41-7.68 |
| 'Cascade' | 5.30 b | 7.16-12.60 |
| 2019 | | |
| 'OR91331' | 11.67 a | 8.65-17.30 |
| 'IH101033' | 11.65 a | 9.91-13.36 |
| 'Sterling' | 8.73 a | 6.75-10.35 |
| 'Cascade' | 8.06 a | 6.15-12.40 |
| 2020 | | |
| 'IH101033' | 15.59 a | 12.70-16.70 |
| 'Sterling' | 12.33 b | 9.80-13.50 |
| 'OR91331' | 8.55 c | 6.95-10.20 |
| 2021 | | |
| 'IH101033' | 12.58 a | 11.15-13.50 |
| 'Sterling' | 10.06 ab | 6.80-14.10 |
| 'OR91331' | 8.78 b | 7.75-9.65 |

†Means within a year followed by the same letter are not statistically significant at P = 0.05.

As shown in Tables 2-4 below, 'IH101033' has lower alpha acids content than 'Cascade' and 'OR91331', and occasionally lower than 'Sterling'. Tables 2-4 also show that 'IH101033' typically has higher beta acids than 'Cascade', 'OR91331', and 'Sterling', and has lower total essential oil content than 'OR91331', but similar to 'Sterling' and 'Cascade'.

TABLE 2

Bittering acids and total oil content in hops grown in Oregon's Willamette Valley during 2017.

| Genotype | | Range |
|---|---|---|
| | Alpha Acids | |
| 'Cascade' | 7.09 a† | 5.68-7.75 |
| 'Sterling' | 5.72 ab | 5.04-6.33 |
| 'IH101033' | 5.15 b | 4.35-6.80 |
| | Beta Acids | |
| 'IH101033' | 6.90 a | 3.99-8.12 |
| 'Cascade' | 5.75 ab | 5.32-6.34 |
| 'Sterling' | 4.06 b | 3.35-4.70 |

TABLE 2-continued

Bittering acids and total oil content in hops grown in Oregon's Willamette Valley during 2017.

| Genotype | | Range |
|---|---|---|
| | Total Oil | |
| 'Sterling' | 2.54 a | 2.18-2.91 |
| 'IH101033' | 1.84 b | 1.78-1.99 |
| 'Cascade' | 1.71 b | 1.18-2.13 |
| | HSI | |
| 'Sterling' | 0.29 a | 0.27-0.31 |
| 'Cascade' | 0.24 b | 0.21-0.26 |
| 'IH101033' | 0.22 b | 0.22-0.23 |
| | Cohumulone | |
| 'Cascade' | 0.353 a | 0.34-0.37 |
| 'Sterling' | 0.220 b | 0.21-0.24 |
| 'IH101033' | 0.183 c | 0.17-0.19 |
| | Colupulone | |
| 'Cascade' | 0.530 a | 0.52-0.54 |
| 'Sterling' | 0.465 b | 0.43-0.48 |
| 'IH101033' | 0.430 c | 0.42-0.45 |

†Means within a chemical compound followed by the same letter are not statistically significant at P = 0.05.

TABLE 3

Bittering acids and total oil content in hops grown in Oregon's Willamette Valley during 2019.

| Genotype | | Range |
|---|---|---|
| | Alpha Acids | |
| 'OR91331' | 12.44 a† | 12.16-12.61 |
| 'Cascade' | 7.11 b | 6.48-7.45 |
| 'Sterling' | 5.84 c | 5.54-6.13 |
| 'IH101033' | 5.12 c | 4.54-6.18 |
| | Beta Acids | |
| 'IH101033' | 9.65 a | 8.39-10.33 |
| 'Cascade' | 6.86 b | 6.50-7.23 |
| 'OR91331' | 5.44 c | 5.35-5.57 |
| 'Sterling' | 4.51 c | 4.38-4.57 |
| | Total Oil | |
| 'Sterling' | 2.21 a | 2.13-2.35 |
| 'OR91331' | 2.02 a | 1.94-2.18 |
| 'Cascade' | 1.95 a | 1.84-2.06 |
| 'IH101033' | 1.87 a | 1.60-2.17 |
| | HSI | |
| 'Sterling' | 0.250 a | 0.25-0.25 |
| 'IH101033' | 0.233 ab | 0.22-0.25 |
| 'OR91331' | 0.223 bc | 0.22-0.23 |
| 'Cascade' | 0.210 c | 0.20-0.22 |
| | Cohumulone | |
| 'Cascade' | 0.355 a | 0.35-0.36 |
| 'Sterling' | 0.253 b | 0.24-0.26 |
| 'IH101033' | 0.240 bc | 0.22-0.26 |
| 'OR91331' | 0.223 c | 0.21-0.23 |
| | Colupulone | |
| 'Cascade' | 0.550 a | 053-0.57 |
| 'Sterling' | 0.447 b | 0.44-0.45 |
| 'OR91331' | 0.443 b | 0.44-0.45 |
| 'IH101033' | 0.410 c | 0.39-0.43 |

†Means within a chemical compound followed by the same letter are not statistically significant at P = 0.05.

TABLE 4

Bittering acids and total oil content in hops grown in Oregon's Willamette Valley during 2020.

| Genotype | | Range |
|---|---|---|
| | Alpha Acids | |
| 'OR91331' | 12.18 a† | 11.58-12.77 |
| 'Sterling' | 6.78 b | 6.33-7.24 |
| 'IH101033' | 3.77c | 3.47-3.99 |
| | Beta Acids | |
| IH101033' | 8.30 a | 7.74-8.66 |
| 'OR91331' | 5.26 b | 4.75-5.55 |
| 'Sterling' | 4.88 b | 3.88-6.05 |
| | Total Oil | |
| 'OR91331' | 2.36 a | 2.06-2.59 |
| 'IH101033' | 1.85 b | 1.75-2.02 |
| 'Sterling' | 1.56 b | 1.26-1.75 |
| | HSI | |
| 'Sterling ' | 0.25 a | 0.23-0.27 |
| 'IH101033' | 0.24 a | 0.22-0.25 |
| 'OR91331' | 0.22 a | 0.19-0.25 |
| | Cohumulone | |
| 'Sterling' | 0.250 a | 0.23-0.29 |
| 'OR91331' | 0.228 ab | 0.21-0.24 |
| 'IH101033' | 0.197 b | 0.18-0.21 |
| | Colupulone | |
| 'OR91331' | 0.488 a | 0.46-0.52 |
| 'IH101033' | 0.420 b | 0.40-0.44 |
| 'Sterling' | 0.400 b | 0.38-0.41 |

†Means within a chemical compound followed by the same letter are not statistically significant at P = 0.05.

Tables 5-7 below show that 'IH101033' contains differing amounts of 19 essential oil components implicated in beer flavor and aroma compared to 'Sterling', 'Cascade', and 'OR91331'.

TABLE 5

Essential oil component concentrations for three hop genotypes grown in Oregon's Willamette Valley in 2017. Data are mg/100 g dried tissue.

| Component | 'IH101033' | 'Sterling' | 'Cascade' |
|---|---|---|---|
| a-Pinene | 1.100 b† | 2.563 a | 1.798 ab |
| b-Pinene | 13.858 b | 26.590 a | 17.545 b |
| Myrcene | 1138.912 b | 2032.755 a | 1311.810 b |
| Limonene | 7.983 b | 15.390 a | 11.780 ab |
| Cymene | 6.780 b | 10.645 a | 3.825 b |
| Methyl Heptanoate | 5.583 b | 2.185 b | 11.700 a |
| Linalool | 17.315 ab | 23.305 a | 11.243b |
| b-Caryophyllene | 112.293 a | 142.763 a | 148.178 a |
| Terpin-4-ol | 0.120 b | 0.263 a | 0.230 a |
| Farnesene | 152.130 a | 128.520 ab | 14.175 b |
| Humulene | 711.265 ab | 887.533 a | 511.450 b |
| Citral 1 | 0.368 b | 0.908 a | 0.130 b |
| Citral 2 | 0.495 b | 1.323 a | 1.213 a |
| a-Terpineol | 0.123 a | 0.188 a | 0.220 a |
| Geranyl Acetate | 1.165 a | 1.123 a | 0.000 b |
| Nerol | 0.775 b | 2.175 a | 1.863 a |
| Geraniol | 2.698 a | 1.953 a | 4.118 a |
| Caryophyllene Oxide | 1.580 a | 2.605 a | 2.005 a |
| Epoxide 2 | 4.363 a | 6.483 a | 5.755 a |

†Means within a chemical compound followed by the same letter are not statistically significant at P = 0.05.

TABLE 6

Essential oil component concentrations for four hop genotypes grown in Oregon's Willamette Valley in 2019. Data are mg/100 g dried tissue.

| Component | 'IH101033' | 'Sterling' | 'Cascade' | 'OR91331' |
|---|---|---|---|---|
| a-Pinene | 1.383 c† | 2.013 b | 2.753 a | 1.583 c |
| b-Pinene | 25.323 b | 32.123 a | 29.840 ab | 24.750 b |
| Myrcene | 1585.27 b | 1720.08 ab | 1947.37 a | 1230.19 c |
| Limonene | 11.613 b | 19.940 a | 18.675 a | 13.883 b |
| Cymene | 11.010 a | 11.387 a | 6.245 b | 11.523 a |
| Methyl Heptanoate | 13.760 b | 5.697 c | 15.598 b | 29.590 a |
| Linalool | 27.283 a | 24.890 a | 14.163 b | 17.147 b |
| b-Caryophyllene | 117.58 c | 166.58 b | 125.50 bc | 315.34 a |
| Terpin-4-ol | 0.323 a | 0.367 a | 0.283 a | 0.230 a |
| Farnesene | 99.800 a | 0.810 b | 76.505 a | 0.370 b |
| Humulene | 726.54 b | 1107.88 a | 384.47 c | 704.42 b |
| Citral 1 | 0.243 c | 1.403 a | 0.080 c | 0.467 b |
| Citral 2 | 0.910 b | 0.963 b | 1.158 b | 1.633 a |
| a-Terpineol | 0.227 b | 0.148 b | 1.373 a | 0.127 b |
| Geranyl Acetate | 1.160 b | 1.790 b | 35.955 a | 4.053 b |
| Nerol | 1.520 b | 1.417 b | 1.810 b | 5.483 a |
| Geraniol | 2.003 b | 5.113 a | 4.533 a | 1.730 b |
| Caryophyllene Oxide | 0.347 c | 0.923 b | 0.773 b | 1.830 a |
| Epoxide 2 | 4.223 b | 6.093 ab | 4.663 b | 8.330 a |

†Means within a chemical compound followed by the same letter are not statistically significant at P = 0.05.

TABLE 7

Essential oil component concentrations for three hop genotypes grown in Oregon's Willamette Valley in 2020. Data are mg/100 g dried tissue.

| Component | 'IH101033' | 'Sterling' | 'OR91331' |
|---|---|---|---|
| a-Pinene | 1.637 ab† | 1.298 b | 2.335 a |
| b-Pinene | 25.830 a | 18.720 a | 24.848 a |
| Myrcene | 1602.673 a | 1103.338 a | 1583.987 a |
| Limonene | 9.970 a | 8.660 a | 12.310 a |
| Cymene | 10.177 a | 6.095 b | 13.488 a |
| Methyl Heptanoate | 15.293 b | 2.643 c | 38.218 a |
| Linalool | 29.713 a | 16.055 c | 22.088 b |
| b-Caryophyllene | 100.070 c | 147.790 b | 358.333 a |
| Terpin-4-ol | 0.557 a | 0.398 a | 0.563 a |
| Farnesene | 131.163 a | 0.000 b | 0.000 b |
| Humulene | 708.920 a | 874.945 a | 776.305 a |
| Citral 1 | 0.360 a | 0.638 a | 0.473 a |
| Citral 2 | 0.950 a | 1.083 a | 0.645 b |
| a-Terpineol | 2.560 a | 1.905 a | 2.378 a |
| Geranyl Acetate | 1.067 b | 1.473 b | 3.995 a |
| Nerol | 1.210 b | 1.268 b | 6.905 a |
| Geraniol | 1.190 b | 6.210 a | 2.303 b |
| Caryophyllene Oxide | 0.353 c | 0.818 b | 1.863 a |
| Epoxide 2 | 6.760 a | 8.253 a | 4.688 a |

†Means within a chemical compound followed by the same letter are not statistically significant at P = 0.05.

SUMMARY OF MORPHOLOGICAL TRAITS

Tables 8, 9, and 10 summarize the principal morphological characteristics of 'IH101033' and how they may differ from 'Sterling' (female parent) and the standard Oregon aroma hop cultivar 'Cascade'. When grown in Oregon's Willamette Valley, 'IH101033':

1. has a wider cone than 'Cascade' (Table 8);
2. has narrower and shorter bracts than the female parent 'Sterling', and shorter bracts than 'Cascade' (Table 8);
3. has shorter and wider bracteoles than 'Sterling' and 'Cascade' (Table 8);
4. has longer mid-canopy main bine internode length than 'Cascade' and 'Sterling' (Table 9); and
5. has a longer and wider leaf than 'Sterling' and 'Cascade' (Table 9).

Figure 2:
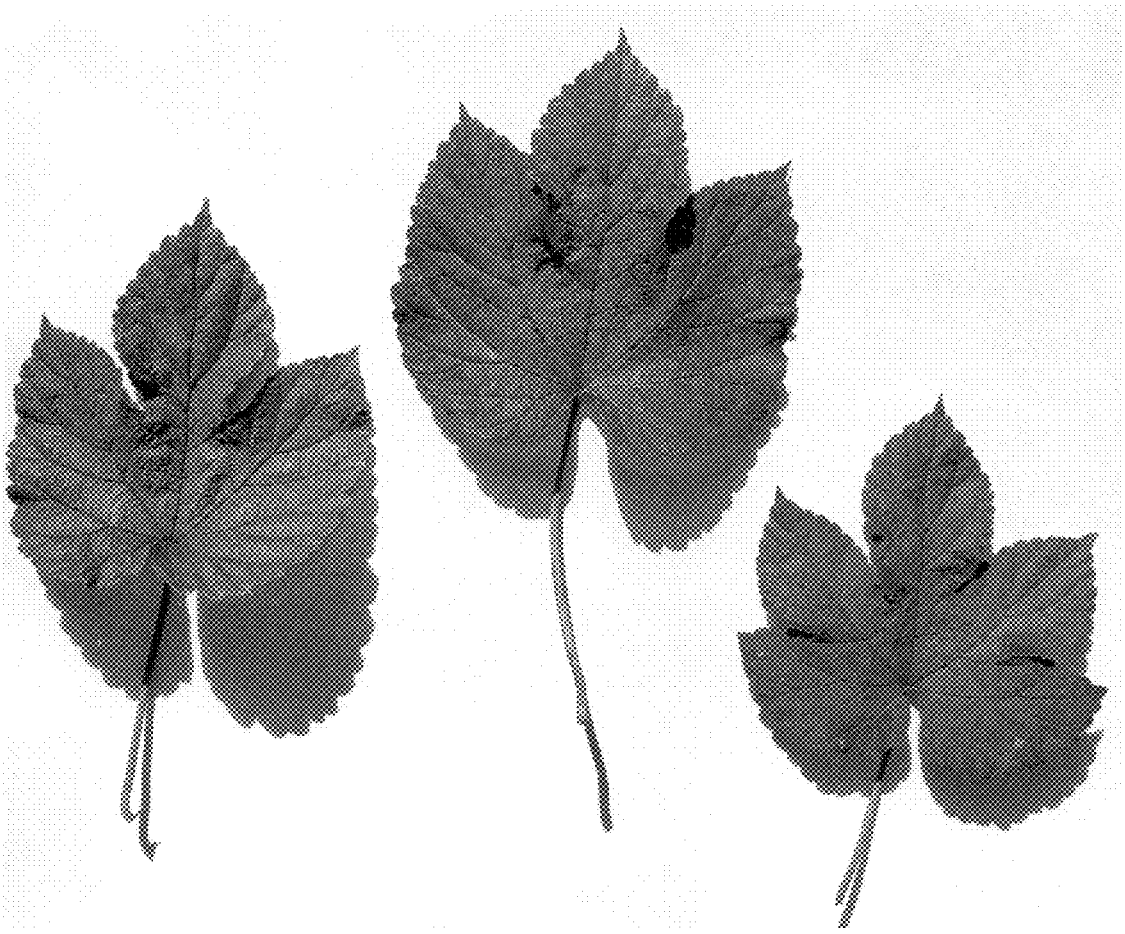
FIG. 2 shows the typical 3-lobe and 5-lobe shapes of mature leaves of 'IH101033'.
Figure 3:
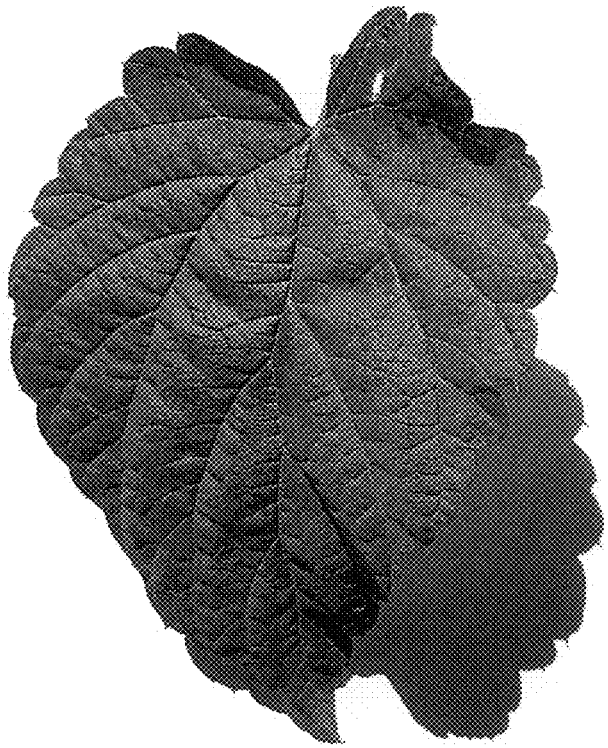
FIG. 3 shows the cordate shape of an immature leaf of 'IH101033'.
Figure 4:
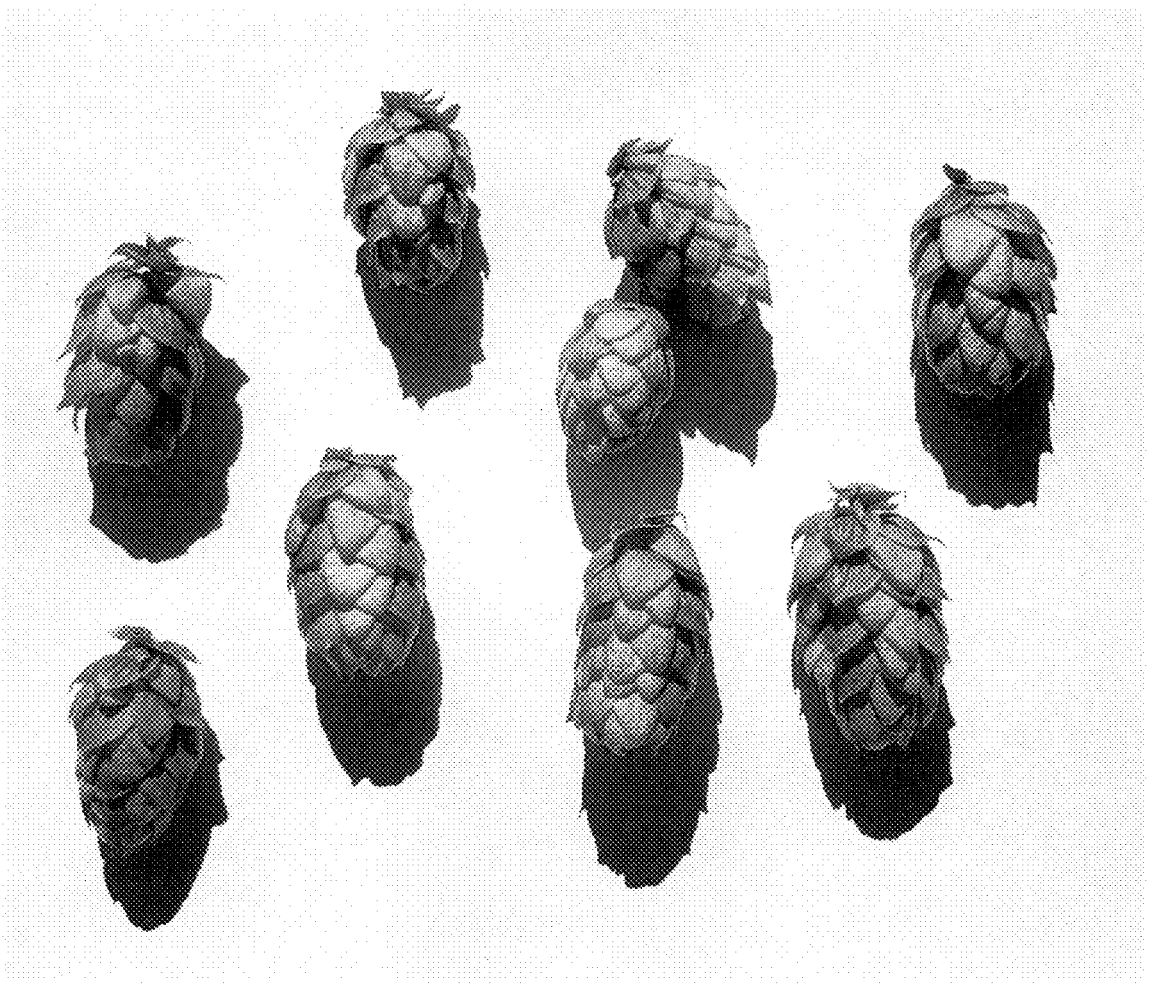
FIG. 4 shows typical hop cones for 'IH101033'.

Additional morphological characteristics are presented in Table 10, while characteristic leaf and cone shapes are presented in FIGS. 2-4. 'IH101033' is slightly earlier to mature (August 22-24) than the female parent 'Sterling' (August 30-September 1), and earlier than 'Cascade' (September 1-5). In addition, 'IH101033' is tolerant of downy mildew (similar to 'Sterling') where 'Cascade' and 'OR91331' are considered resistant.

TABLE 8

Cone measurements for 'IH101033', its female parent 'Sterling', and an industry-standard aroma hop cultivar 'Cascade' when grown in Oregon's Willamette Valley.

| Genotype | Trait | Range |
|---|---|---|
| | Cone Bract Width (cm) | |
| 'Sterling' | 1.19 a | 0.80-1.50 |
| 'Cascade' | 1.16 a | 0.90-1.30 |
| 'IH101033' | 1.04 b | 0.20-1.20 |
| | Cone Bract Length (cm) | |
| 'Sterling' | 2.00 a | 1.60-2.30 |
| 'Cascade' | 1.81 b | 1.30-2.10 |
| 'IH101033' | 1.63 c | 1.00-2.00 |
| | Cone Bracteole Width (cm) | |
| 'IH101033' | 1.52 a | 1.30-1.80 |
| 'Cascade' | 0.99 b | 0.50-1.30 |
| 'Sterling' | 0.99 b | 0.80-1.10 |
| | Cone Bracteole Length (cm) | |
| 'Sterling' | 1.80 a | 1.00-2.10 |
| 'Cascade' | 1.69 b | 1.00-2.10 |
| 'IH101033' | 0.89 c | 0.70-1.00 |
| | Cone Length (cm) | |
| 'IH101033' | 4.10 a | 3.00-5.20 |
| 'Cascade' | 3.67 a | 3.20-4.70 |
| | Cone Width (cm) | |
| 'IH101033' | 2.17 a | 1.80-2.90 |
| 'Cascade' | 1.90 b | 1.70-2.40 |

TABLE 9

Morphological measurements for 'IH101033' and two additional aroma hop genotypes grown in the Oregon's Willamette Valley.

| Genotype | Trait | Range |
|---|---|---|
| | Main Bine Internode Length (cm) | |
| 'IH101033' | 24.46 a | 20.00-28.20 |
| 'Sterling' | 21.46 b | 16.40-26.20 |
| 'Cascade' | 20.42 b | 16.20-23.40 |
| | Main Bine Diameter (mm) | |
| 'Cascade' | 7.4 a | 4.0-11.0 |
| 'IH101033' | 7.2 a | 5.00-9.00 |
| 'Sterling' | 7.1 a | 5.00-9.00 |
| | Petiole Length (cm) | |
| 'Cascade' | 8.68 a | 5.80-11.90 |
| 'IH101033' | 8.00 ab | 6.80-11.50 |
| 'Sterling' | 6.99 b | 4.30-9.50 |
| | Leaf Width (cm) | |
| 'IH101033' | 15.44 a | 11.50-17.50 |
| 'Sterling' | 13.39 b | 10.70-15.50 |
| 'Cascade' | 12.77 b | 10.3-14.50 |

TABLE 9-continued

Morphological measurements for 'IH101033' and two additional aroma hop genotypes grown in the Oregon's Willamette Valley.

| Genotype | Trait | Range |
|---|---|---|
| | Leaf Length (cm) | |
| 'IH101033' | 16.47 a | 13.60-19.10 |
| 'Cascade' | 14.11 b | 12.70-16.00 |
| 'Sterling' | 13.45 b | 10.50-15.10 |
| | Sidearm Length (cm) | |
| 'Cascade' | 78.95 a | 51.10-129.50 |
| 'IH101033' | 74.96 a | 55.80-94.20 |
| 'Sterling' | 59.12 a | 32.10-104.50 |
| | Sidearm Internode Length (cm) | |
| 'IH101033' | 9.38 a | 6.50-13.50 |
| 'Cascade' | 8.65 a | 3.10-15.80 |
| 'Sterling' | 7.70 a | 3.60-14.30 |

TABLE 10

Morphological characteristics for the hop genotype 'IH101033' when grown in Oregon's Willamette Valley.

| Trait | Descriptor |
|---|---|
| Ploidy | 2X (diploid) |
| Plant | Vigorous climbing bine |
| Shape | Columnar |
| Plant head volume | High |
| Target area | Oregon's Willamette Valley (USDA hardiness zone 8b near latitude 45 degree North) |
| Bine | |
| Color | 145D |
| Anthocyanin coloration | 184C |
| Mid-canopy internode Length (cm) | Average = 24.46, Range = 20.0-28.2 |
| Diameter (mm) | Average = 7.2, Range = 5.0-9.0 |
| Total Length (ft) | 21 |
| Sidearm | |
| Mid-canopy length | Medium (55.8-94.2 cm) |
| Petiole | |
| Length (cm) | Average = 8.0, Range = 6.8-11.5 |
| Color | 181A top, N144C bottom |
| Shape | Flat upper surface with channel |
| Leaf | |
| Arrangement | Opposite |
| Shape | Immature = cordate, mature = mix of 3-lobed and 5-lobed |
| Adaxial leaf texture | pubescent |
| Abaxial leaf texture | pubescent, particularly along veins |
| Color | Upper = NN137A, lower = NN137D |
| Mature leaf width (cm) | Average = 15.44, Range = 11.5-17.5 |
| Mature leaf length (cm) | Average = 16.47, Range = 13.6-19.1 |
| Leaf lobing | Immature = cordate, mature = mix of 3-lobed and 5-lobed |
| Venation | primary order: palmate<br>secondary order: craspedodromous |
| Vein color | Upper = 146A, lower = 146B |
| Blistering | Absent |
| Leaf margin | Serrated |
| Lateral length, mid-canopy (cm) | Average = 74.96, Range = 55.8-94.2 |

TABLE 10-continued

Morphological characteristics for the hop genotype 'IH101033' when grown in Oregon's Willamette Valley.

| Trait | Descriptor |
|---|---|
| Lateral internode length (cm) | Average = 9.38, Range = 6.5-13.5 |
| Blistering | None |
| Cone | |
| Shape | Medium ovate |
| Flowering date | July 10-20 |
| Maturity date | August 22-24 |
| Coning abundance | Mid-canopy cone number: Many<br>Upper-canopy cone number: Many |
| Length (cm) | Average = 4.10, Range = 3.0-5.2 |
| Width (cm) | Average = 2.17, Range = 1.8-2.9 |
| Number of bracts per cone | Average = 29.2, Range = 22-36 |
| Number of bracteoles per cone | Average = 48.5, Range = 40-60 |
| Total bracts + bracteoles per cone | Average = 77.7, Range = 62-96 |
| Bract color | 145A |
| Bract length (cm) | Average = 1.63, Range = 1.0-2.0 |
| Bract width (cm) | Average = 1.04, Range = 0.2-1.2 |
| Bract apex length (mm) | Average = 2.03, Range = 1.0-3.0 |
| Bracteole length (cm) | Average = 0.89, Range = 0.7-1.0 |
| Bracteole width (cm) | Average = 1.52, Range = 1.3-1.8 |
| Bracteole color | 145A |

COMPARISON TO MALE PARENT '64035M'

The male parent, '64035M', was released by the USDA in 1984 as a downy mildew-resistant male genotype for breeding purposes. It derives from open-pollinated seed collected off of the German female hop 7K491 at Wye College, England. Key differences between 'IH101033' and its' male parent '64035M' include:

1. 'IH101033' is a female genotype and only produces female flowers while '64035M' is a male genotype and only produces male flowers
2. 'IH101033' is tolerant of downy mildew while '64035M' is considered resistant.

SENSORY OBSERVATIONS

Beginning in September 2017, sensory evaluations by small, organized groups of craft brewers were initiated. To date, 96 brewers have participated in dry-rub evaluations and small-scale test beers in which 'IH101033' was dosed into a Kolsch-style beer that has no aroma or flavor characteristics. Small-scale test beers were also produced to assess 'IH101033' character on both the hot-side and dry-hopping stage. Typically, the first notes noticed are the citrus notes lemon supported by lime. Brewers report that the initial lemon and lime notes are followed by fresh melon notes (usually honeydew and cantaloupe) and mixed wild-flower floral notes. Additional notes reported include dry grass and cinnamon or baker's spice.

I claim:

1. A new and distinct variety of hop plant named 'IH101033', substantially as illustrated and described herein.

* * * * *